(12) United States Patent
Martz

(10) Patent No.: US 7,240,375 B2
(45) Date of Patent: Jul. 10, 2007

(54) WAISTLESS UNDERWEAR ALTERNATIVE SECRET PANTS SHIELD

(76) Inventor: Christine Martz, 1128 Ruth Pl., North Bellmore, NY (US) 11710

( * ) Notice: Subject to any disclaimer, the term of this patent is extended or adjusted under 35 U.S.C. 154(b) by 0 days.

(21) Appl. No.: 10/813,982

(22) Filed: Mar. 31, 2004

(65) Prior Publication Data

US 2004/0181853 A1   Sep. 23, 2004

Related U.S. Application Data

(60) Provisional application No. 60/459,462, filed on Apr. 1, 2003.

(51) Int. Cl.
  *A41B 9/12* (2006.01)
  *A61F 13/15* (2006.01)
  *A41B 9/00* (2006.01)

(52) U.S. Cl. .................... 2/406; 604/345; 604/353; 604/402

(58) Field of Classification Search .......... 2/400–406; 604/383–400, 402, 358, 345, 353, 354
  See application file for complete search history.

(56) References Cited

U.S. PATENT DOCUMENTS

| | | | |
|---|---|---|---|
| 1,465,076 A | 8/1923 | Dupont | |
| 1,897,952 A | 2/1933 | Dupont | |
| 2,534,934 A | 12/1950 | Viniegra | |
| 3,044,467 A | 7/1962 | Campau | |
| 3,339,208 A | 9/1967 | Marbach | 2/67 |
| 4,227,264 A | 10/1980 | Spector | 2/84 |
| 4,244,368 A | 1/1981 | Caradonna | 128/287 |
| 4,347,092 A | 8/1982 | Hlaban et al. | |
| 4,425,130 A | 1/1984 | DesMarais | |
| 4,518,451 A | 5/1985 | Luceri et al. | |
| 4,605,404 A | 8/1986 | Sneider | |
| 4,648,876 A | 3/1987 | Becker et al. | |
| 4,738,676 A | 4/1988 | Osborn, III | |
| 4,747,162 A | 5/1988 | Yanagihara | |

(Continued)

FOREIGN PATENT DOCUMENTS

CA   2285646   4/2001

(Continued)

OTHER PUBLICATIONS

True Fit Try On® garment liners, Internet page, www.truefittryon.com , 2 pages, showing liners.

*Primary Examiner*—Gloria M. Hale
(74) *Attorney, Agent, or Firm*—Alfred M. Walker; Mark E. Bender

(57) ABSTRACT

A women's waistless and seamless clothing adherable underwear includes an oval pad made of a soft absorbent material, wherein the pad has double sided strips of adhesive tape with removable peel-off cover strips to attach to the inside crotch area of low slung clothing pants, such as tight pants, leotards or dungaree jeans facing upward to the skin and crotch of the wearer. The material is preferably a soft, woven or non-woven, absorbent material. The underwear is particularly suited for women who wear tight pants, or low waist hip hugger pants, which widely reveal waist bands and seams of panty underwear, or expose underwear waist bands. The underwear is minimally intrusive and is attractive for women who like to wear jeans without underwear but who fear bacterial infection or exposure to clothing dyes or irritating stitching.

3 Claims, 5 Drawing Sheets

U.S. PATENT DOCUMENTS

| | | | |
|---|---|---|---|
| 4,834,739 A | 5/1989 | Linker, III et al. | |
| 4,846,829 A | 7/1989 | Lloyd | |
| 4,847,134 A | 7/1989 | Fahrenkrug | 428/138 |
| 4,882,220 A * | 11/1989 | Ono et al. | 442/96 |
| 4,905,323 A | 3/1990 | Lampman | |
| 4,917,920 A * | 4/1990 | Ono et al. | 427/389.9 |
| 4,951,321 A | 8/1990 | Mortensen et al. | |
| 4,955,880 A | 9/1990 | Rodriquez | 604/393 |
| 4,961,234 A | 10/1990 | Leibman | |
| 4,982,450 A * | 1/1991 | D'Huissier | 2/402 |
| 5,010,595 A | 4/1991 | Stradley | 2/227 |
| 5,042,088 A | 8/1991 | Sherrod et al. | |
| 5,072,454 A | 12/1991 | Trahan | 2/70 |
| 5,081,718 A | 1/1992 | Carman | 2/227 |
| 5,095,549 A | 3/1992 | Aldridge | |
| 5,103,501 A | 4/1992 | Meisels | |
| 5,242,632 A | 9/1993 | Mende | 264/6 |
| 5,344,698 A | 9/1994 | Rock | 428/253 |
| 5,347,657 A * | 9/1994 | Unsell | 2/67 |
| 5,367,715 A | 11/1994 | Leonard | 2/401 |
| 5,370,632 A | 12/1994 | Beplate | 604/385.1 |
| 5,415,650 A | 5/1995 | Sigl | |
| 5,467,482 A | 11/1995 | Crawford | 2/67 |
| 5,591,146 A * | 1/1997 | Hasse | 604/359 |
| 5,593,398 A | 1/1997 | Weimer | |
| 5,611,790 A | 3/1997 | Osborn, III et al. | |
| 5,678,251 A * | 10/1997 | Getz | 2/406 |
| 5,729,835 A | 3/1998 | Williams | |
| 5,774,891 A | 7/1998 | Boyer | 2/69 |
| 5,778,457 A | 7/1998 | Conway | |
| 5,807,365 A | 9/1998 | Luceri | |
| 5,832,535 A | 11/1998 | Davis | 2/1 |
| D405,938 S | 2/1999 | Trombetta | |
| 5,884,330 A | 3/1999 | Erlich | |
| 5,903,922 A | 5/1999 | Vargason | 2/78.1 |
| 5,946,730 A | 9/1999 | Blair | 2/227 |
| 6,049,915 A | 4/2000 | Malowaniec | 2/400 |
| 6,049,916 A | 4/2000 | Rajala et al. | |
| 6,067,663 A | 5/2000 | Fernandez | 2/406 |
| 6,093,178 A | 7/2000 | Osborn, III et al. | |
| 6,098,203 A | 8/2000 | Rajala et al. | |
| D434,145 S | 11/2000 | Sugahara | |
| 6,162,457 A | 12/2000 | Martz | 424/448 |
| 6,162,961 A | 12/2000 | Tanner | 604/374 |
| 6,173,449 B1 | 1/2001 | Osterrath | 2/67 |
| 6,176,850 B1 | 1/2001 | Rosenfeld et al. | |
| 6,210,386 B1 | 4/2001 | Inoue | |
| 6,231,558 B1 | 5/2001 | Mosley | |
| 6,232,250 B1 | 5/2001 | Palumbo | 442/389 |
| D443,358 S | 6/2001 | Jonsdottir | |
| 6,240,569 B1 | 6/2001 | Van Gompel et al. | |
| 6,247,184 B1 | 6/2001 | Watts | |
| D444,554 S | 7/2001 | O Hara | |
| 6,260,211 B1 | 7/2001 | Rajala et al. | |
| 6,277,223 B1 | 8/2001 | Herrin et al. | |
| 6,306,122 B1 | 10/2001 | Narawa et al. | |
| 6,307,120 B1 | 10/2001 | Glaug | |
| 6,313,371 B1 | 11/2001 | Conant et al. | |
| 6,315,022 B1 | 11/2001 | Herrin et al. | |
| 6,317,893 B1 | 11/2001 | Walton | 2/227 |
| 6,364,863 B1 | 4/2002 | Yamamoto et al. | |
| 6,367,089 B2 | 4/2002 | Van Gompel et al. | |
| 6,371,831 B1 | 4/2002 | Dodge | 480/81 |
| 6,391,011 B1 | 5/2002 | Davis et al. | |
| 6,392,117 B1 | 5/2002 | Mayer et al. | |
| 6,401,250 B1 | 6/2002 | McNabb | 2/78.2 |
| 6,406,462 B1 | 6/2002 | Johnson | 604/327 |
| 6,490,732 B1 | 12/2002 | Spoke | 2/67 |
| 2002/0184698 A1 | 12/2002 | Harris | 2/400 |
| 2003/0019251 A1 | 1/2003 | Browder | 66/171 |
| 2003/0028162 A1 | 2/2003 | Haarer | 604/358 |
| 2004/0068247 A1 | 4/2004 | Connor | 604/387 |
| 2004/0117895 A1 | 6/2004 | Fortner | 2/267 |

FOREIGN PATENT DOCUMENTS

| | | |
|---|---|---|
| WO | WO 9416655 | 4/1994 |
| WO | WO 0025726 | 11/2000 |

\* cited by examiner

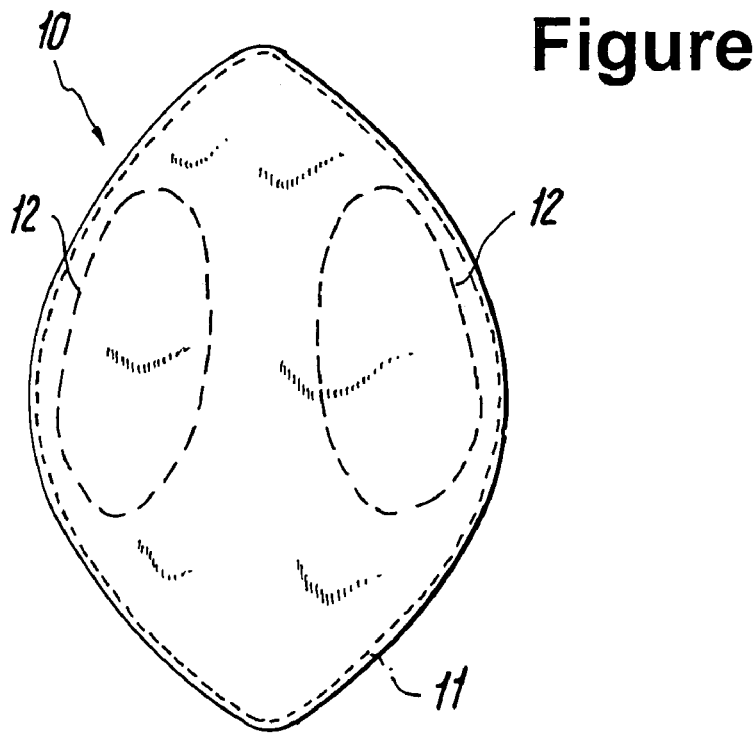
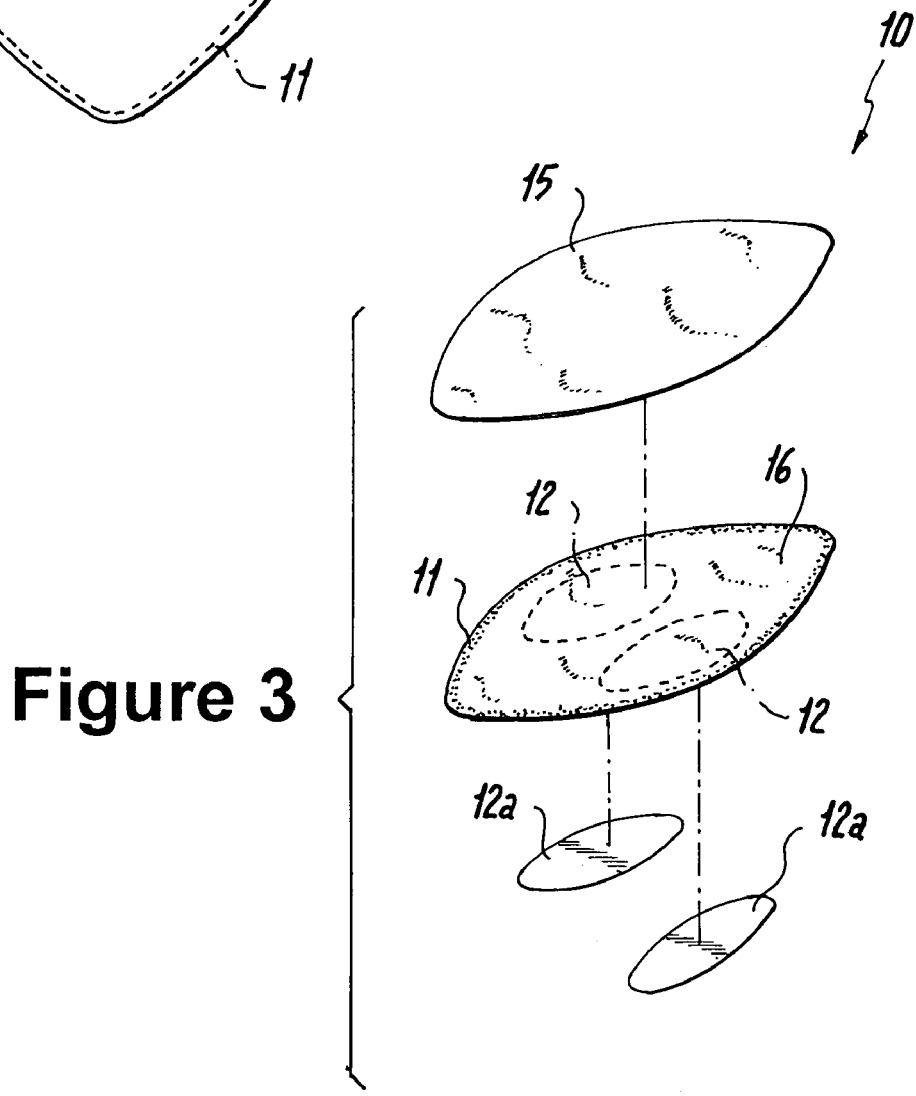

WAISTLESS UNDERWEAR ALTERNATIVE SECRET PANTS SHIELD

RELATED APPLICATIONS

This application is based upon provisional patent application Ser. No. 60/459,462 of Apr. 1, 2003, and claims benefit under 35 USC 119(e). This application is also based in part upon application Ser. No. 10/741,176 of Dec. 20, 2003, which is a continuation of application Ser. No. 10/202,350 of Jul. 24, 2002, now U.S. Pat. No. 6,681,407B2.

FIELD OF THE INVENTION

The present invention relates to disposable waistless and seamless underwear for women.

BACKGROUND OF THE INVENTION

Conventional women's panty underwear with waistbands and seams around the leg openings is unsuitable for women who wear tight pants, or low waist pants (such as "hip huggers"), which openly reveal waist bands and seams of panty underwear, or expose underwear waist bands.

Moreover, for women who like to wear jeans without underwear there is a natural fear of bacterial infection or exposure of sensitive body tissues to clothing dyes or irritating stitching.

Among related prior art patents are those which fall into four categories for which common distinguishing arguments can be composed. The categories are special garments or undergarments, absorbent materials for pads, clothing adhered pads, and maternity wear.

Clothing Adhered Pads:

U.S. Pat. No. 6,162,457 of the Applicant Christine Martz herein describes small clothing adherable perfume patches which attach to the inside of clothing, such as a blouse, with a skin facing side rubbing intermittently against the skin, to mute the smell of the perfume emitted by exposure to body oil in the skin of the wearer.

However, neither Martz '457 nor Williams, in U.S. Pat. No. 5,729,835, relate to a pants shield designed to permit the user to comfortably wear jeans, pants or shorts or the like without an undergarment and also without any external indication that such a shield is being used. Martz '457 relates to small garment pads used to emit a fragrance; their general physical shape and construction are different from the instant invention. Williams '835 relates to a panty liner of generally oblong configuration specifically for use with thong underwear. The multilayer construction designed for maximum absorption and a "penetration barrier" would be far too bulky for the objectives of the present invention.

Maternity Wear:

Blair, in U.S. Pat. No. 5,946,730 describes an expansion panel for temporarily providing a larger waist and frontal area so that a user can wear the jeans during pregnancy. The panel is easily removable when it is no longer needed. Clearly this prior art is irrelevant to the present invention.

Absorbent Materials for pads:

Palumbo et al., in U.S. Pat. No. 6,232,250 B1 relates to an absorbent pad with defined fluid receiving and fluid retention regions. It is designed primarily for use in treating female incontinence.

Rock et al., in U.S. Pat. No. 5,344,698 describes a composite undergarment fabric of multilayer construction using a skin contact layer of hydrophilic material with superabsorbent and high moisture transmission layers attached.

Mende, in U.S. Pat. No. 5,242,632 relates to a nonwoven fabric and manufacturing method. It is a soft bulky absorbent and permeable material.

Tanner et al., in U.S. Pat. No. 6,162,961 has an absorbent article having exceptional expansion properties when wetted.

None of the above materials are required in the construction of the present invention. High moisture absorption is not a key requirement. Comfort and low thickness so as to preclude edge detection from external viewing of the outer garment are principal requirements which cannot be supported by the materials described in this group of patents.

Special Garments or Undergarments:

Glaug, in U.S. Pat. No. 6,307,120 B1 describes a cloth-like, breathable disposable brief with refastening means. It is an adult garment for controlling incontinence.

Davis, in U.S. Pat. No. 5,832,535 discloses a genital covering garment that is a minimum temporary covering generally useful for surgical procedures or examinations not requiring visual or tactile access to these regions.

Marbach, in U.S. Pat. No. 3,339,208 relates to a minimal covering for the lower part of the anatomy consisting of a spring supported patch that fits between the user's legs and engages the pubic bone and the sacrum. The intended use is as a bathing brief.

Crawford, II, in U.S. Pat. No. 5,467,482 describes a self supporting sideless and waistless tanning brief. This is a malleable wire frame with a cloth covering extending to the rear with a spring member which fits between the buttocks of the wearer.

Vargason, in U.S. Pat. No. 5,903,922 discloses a removable undergarment that is designed for quick wearing. A variety of attachment patches are used to attach the undergarment around the user in a comfortable fashion.

Lampman, in U.S. Pat. No. 4,905,323 describes a disposable undergarment held by a partially encircling belt, wherein the undergarment covers the pubic area and central buttocks of the user. It can be used by women while trying on bathing suits or the like in stores.

The inventions in this group relate to garments or undergarments. None disclose a clothing attached secret shield that can be used as a substitute to using an undergarment.

OBJECTS OF THE INVENTION

It is therefore an object of the present invention to provide underwear for women which is suitable for wearing with low slung hip hugging pants and the like.

It is also an object of the present invention to provide waistless and seamless underwear for garments which utilizes a sanitary absorbent material and which prevents irritation or exposure to bacteria and other pathogens.

Other objects which become apparent from the following description of the present invention.

SUMMARY OF THE INVENTION

In keeping with these objects and others which may become apparent, the present invention is a pants shield that is invisible from the exterior and which can be used with any form-fitting attire without the use of underpants or any undergarment.

Since the pants shield is adherable only to the upper crotch facing area of an outer pants garment, it is unencumbered by auxiliary supports, such as annoying skin adhering adhesives or other body supports, such as waistbands, belts, or buttocks holding supports.

Some current fashions for young women are such that they render normal underpants or even thongs undesirable, but the alternative of not wearing underwear has its own disadvantages.

Constructed of a thin absorbent pad, the pants shield of the present invention is adhesively bonded temporarily during use to the crotch area of the outer garment. It can be used in jeans, exercise pants, leotards, shorts, or any normal pants. This permits active use of the garment without underpants which introduce seams and hems that show through as panty lines. This secret pants shield is more comfortable than a thong and more fashionable because low cut pants often reveal the top band of the thong when bending or stretching. Because of the soft shield surface in contact with vaginal area, it prevents infections that can arise from abrasion or irritation caused by rubbing against clothing materials when underpants are not worn. The shield of this invention provides a clean bacteria-free barrier from garment fabric which may also contain irritating dyes. It absorbs small amounts of moisture and also provides extra protection for garments during menstruation periods without the need for an undergarment.

Therefore this secret pants shield permits sanitary wear of pants without underwear providing the ultimate fashion compatibility with any pants attire. Comfort is provided by the soft contact material. Since it is securely bonded with a temporary adhesive, it can be used for active pursuits. The disposable nature and small compact size makes it convenient to change a shield whenever it gets messy. The secret pants shields are available in different sizes such as small, medium, and large. They are also available in colors so as not to contrast with the color of pants which may be shear or slightly transparent.

As an alternative to panties, an undergarment includes an absorbent pad over the genital area which is held in place by a light weight stretch fabric (such as lace) strap. The distal ends of the strap are attached to nonallergenic adhesive patches which adhere to the skin in front and back for attachment.

This garment can be fabricated either as a disposable or reusable panty alternative. In a disposable version, the back adhesive patch is permanently attached (as by sewing or adhesive) to the stretch fabric strap. The front patch is attached to the strap via a hook and loop attachment that facilitates detachment of the strap from the front adhesive patch without removing the adhesive patch from its skin attachment; this is primarily to accommodate toileting.

In a reusable version, the part that is washable and therefore reused is the strap which can then afford to be more substantial and decorative than that of a disposable version. In this case, both adhesive patches are removable via a hook and loop attachment to the strap so that new adhesive patches are attached for each use. A new pad is also attached via pressure sensitive adhesive for each use. The adhesive patches in this embodiment can optionally have a decorative outer covering of fragrance emitting fabric.

In an alternative embodiment, the panty alternative also uses an absorbent pad over the genital area. It is held in place inside an extremely scant panty-like garment. Since the height of the garment is too short to fit over the hips for secure positioning, adhesive patches are used.

These patches can be placed on the inside of the garment to attach to the user's body, or they can be placed on the outside surface of the garment to attach to the user's outer garment if pants are worn. This embodiment can also be fabricated as a reusable cotton garment with replaceable adhesive patches and pad, or it can be fabricated as a disposable of cotton fabric, woven or non-woven synthetic fabric, or even paper.

BRIEF DESCRIPTION OF THE DRAWINGS

The present invention can best be understood in connection with the accompanying drawings. It is noted that the invention is not limited to the precise embodiments shown in drawings, in which:

FIG. 2 is a top view of a secret pants shield of this invention;

FIG. 3 is an perspective exploded view of the pants shield of FIG. 2;

DETAILED DESCRIPTION OF THE INVENTION

Figure 1:
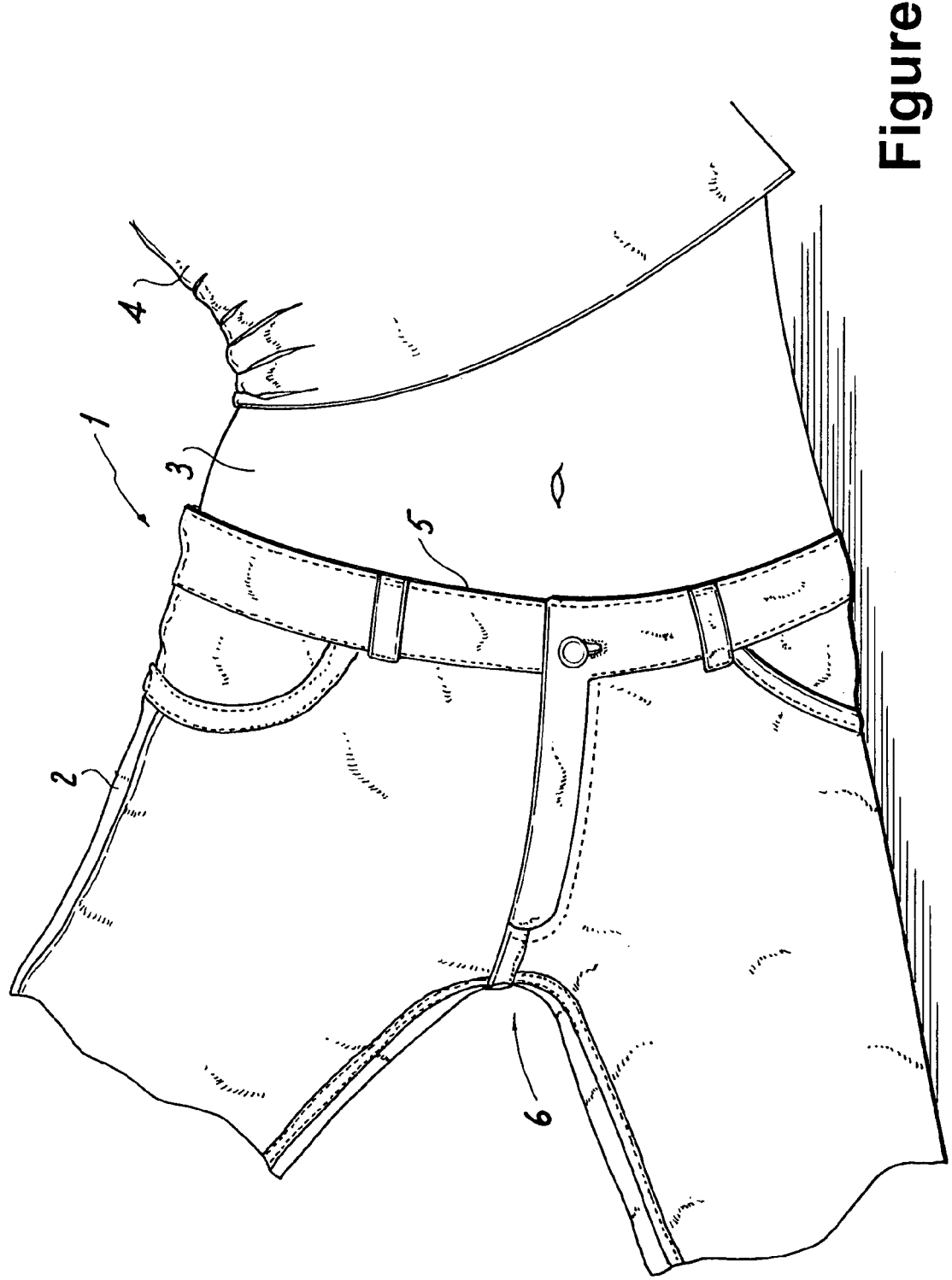
FIG. 1 is a partial perspective view of a reclining woman wearing form-fitting jeans.

FIG. 1 shows a detail of a reclining woman 1 wearing an ensemble which derives maximum benefit from the secret pants shield of this invention. Several features of the style conspire to make the use of underwear undesirable. Jeans 2 are tight and form-fitting with low hip-hugging waist band 5. The short top 4 leaves a bare abdominal midriff 3. This exposed central area is antithetical to underwear waistbands. The site of the secret pants shield of this invention is crotch area 6 which is not disturbed by any indication of the shield within.

FIG. 2 shows pants shield pad 10 with circumferentially extending bonded edge 11 and bottom adhesive areas 12. While FIG. 2 shows two bottom adhesive areas, one or more adhesive areas can be employed to adhere pants shield pad 10 to an inside crotch facing portion of a pants garment.

The exploded view of FIG. 3 reveals the construction with top layer 15, adhesive ring 11 around bottom layer 16, adhesive areas 12 and release liners 12a which cover adhesive patches 12 until use. The top layer 15 is a soft absorbent paper material such as soft paper towel. The bottom layer 16 can be identical material. Adhesive ring 11 bonds layers 15 and 16 permanently. Adhesive 12 is a temporary adhesive analogous to that used on feminine hygiene panty liner pads. An alternate construction of a single layer equivalent to the two layers of soft paper towel can also be used. Moreover, one or more adhesive layers 12 can be employed to attach pants shield pad 20 to a crotch facing area of pants garment.

A prototype for one embodiment for a secret pants shield has been constructed and tested successfully. Layers 15 and 16 were cut out of KLEENEX® VIVA® paper towel, and the adhesive areas 12 were double width lengths of ¾" wide SCOTCH® Poster Tape from 3M Company.

Figure 4:
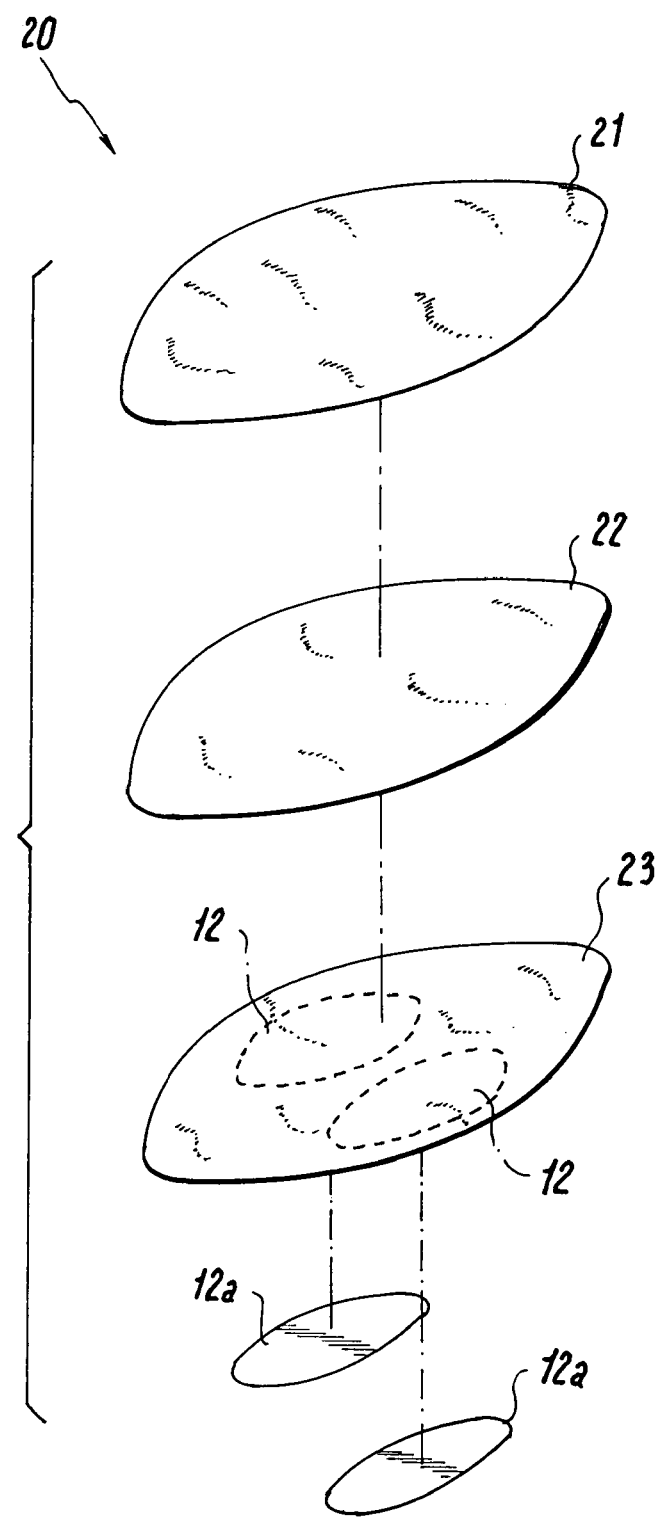
FIG. 4 is a perspective exploded view of a different embodiment of a pants shield.

FIG. 4 shows the construction of alternate embodiment 20 of the secret panty shield of this invention. It includes at least three surface bonded layers with adhesive patches on the bottom layer. Top layer 21 is a thin permeable nonwoven fabric material, such as of a paper or a synthetic plastic material. However, top layer 21 may also be a woven material. Middle layer 22 is a thin absorbent non-woven or woven material, and bottom layer 23 is a thin impermeable layer, such as of paper or of a synthetic plastic. Adhesive patches 12 with release liners 12a complete shield 20. The construction and materials of the various layers are similar to those of a light weight bed pad.

The bottom layers 16 or 23 adjacent to the transparent temporary adhesive patches 12 can be selected in a variety of colors to minimize contrast with pants material.

Total thickness of the secret pants shield must be kept to a minimum to prevent a visible outline from showing through. For context, it is well to know that panty seams range from a thickness of about 0.08" (2 mm) to about 0.12" (3 mm) and are quite visible under tight pants. A LIGHT-DAYS™ feminine hygiene pad from KOTEX® is 0.075" (1.9 mm). The thickness of the preferred embodiment of secret pants shield as in FIG. 3 (with two layers) is about 0.030" (0.76 mm). The thickness of the second embodiment as in FIG. 4 (with three layers) is 0.025" (0.64 mm). The secret pants shield of this invention is therefore preferably less than 1 mm thick, which is not visible externally.

Figure 5:
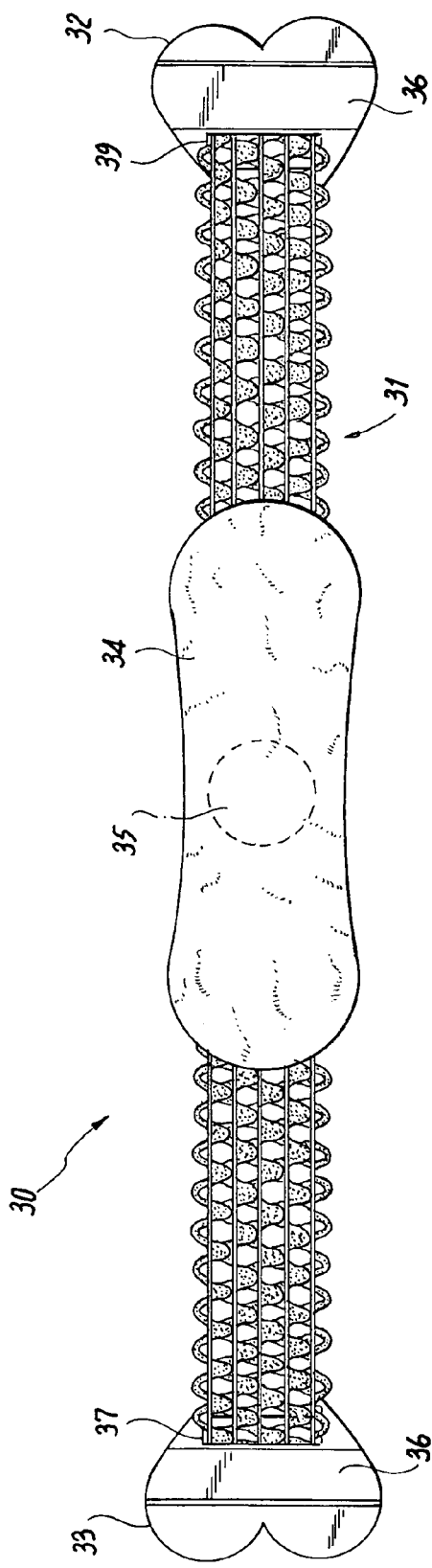
FIG. 5 is a top plan view of an inner side of a panty alternative of this invention.

FIG. 5 shows the inner surface of panty alternative 30 of an alternate embodiment.

Figure 6:
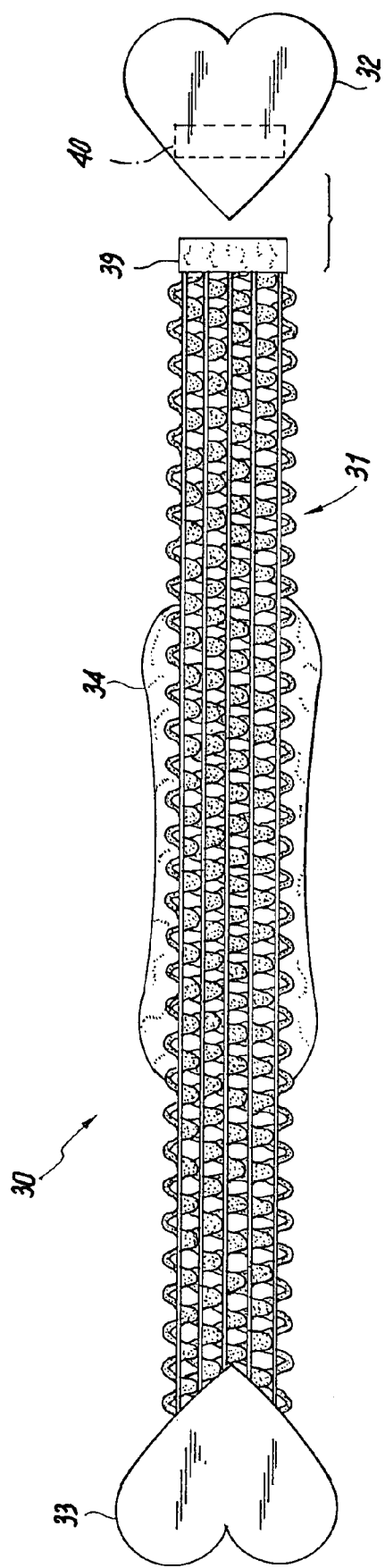
FIG. 6 is a top plan view of an outer side of the panty alternative as in FIG. 5.
Figure 7:
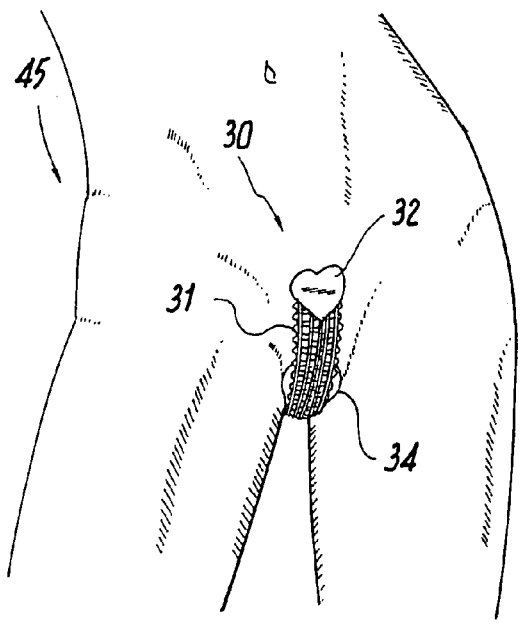
FIG. 7 is a front elevational view detail of a model wearing the panty alternative as in FIG. 5.
Figure 8:
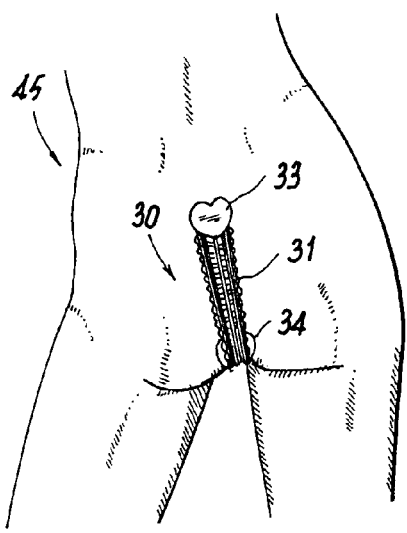
FIG. 8 is a rear view detail of the model wearing the panty alternative as in FIG. 5.

FIG. 6 shows the outer surface, while FIGS. 7 and 8 show the front and back view respectively of a model wearing panty alternative 30. Panty alternative 30 includes stretch fabric strap 31, absorbent pad 34 and adhesive patches 32 for the front and 33 for the back.

In use, adhesive patches 32 and 33 are attached to the user's skin as shown in the model 45 details of FIGS. 7 and 8. The underside of patch 32 and 33 has a nonallergenic adhesive covered by release liner 36 which is removed prior to attachment.

Since a disposable version is shown in FIGS. 5 and 6, rear patch 33 is permanently attached to strap 31 by stitching 37 or adhesive. Front patch 32 has a small area of loop material 40 which engages a corresponding area of hook material which is adhesively attached (or stitched) to strap 31. This facilitates removal of the garment for toileting purposes with easy reattachment without removal of the adhesive from the skin. The decorative top covering of adhesive patches 32 and 33 can optionally be an outer fragrance emitting layer. Absorbent pad 34 is attached to strap 31 by adhesive patch 35.

Pad 34 can be a light cotton panel or a paper product similar to a sanitary pad. For a version where strap 31 is reusable and washable, old pad 34 is replaced with each use as are adhesive attachment pads 32 and 33. For a reusable version, patch 33 would be attached to strap 31 in the same manner as shown in FIG. 6 for patch 32.

Figure 9:
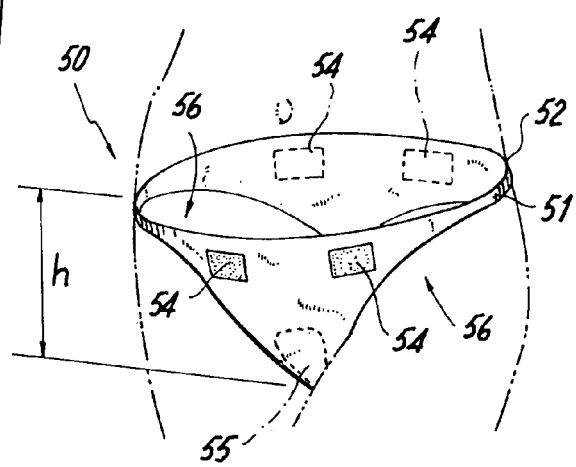
FIG. 9 is a perspective view of an alternative embodiment of the panty alternative using adhesive patches on an outer surface; and, FIG. 10 is a perspective view of a further alternative embodiment using adhesive patches on an inner surface.
Figure 10:
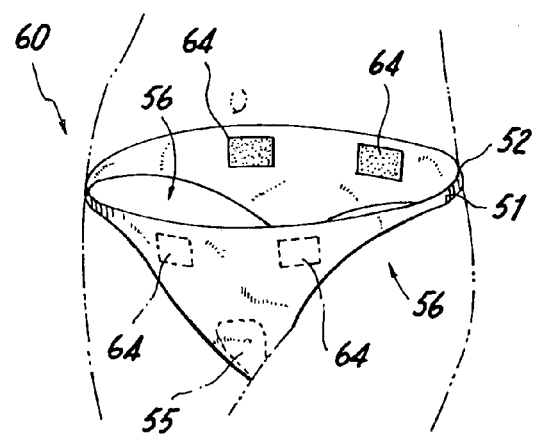

In an alternate embodiment, absorbent pad 55 is adhesively attached to a panty-like garment 51 as shown in FIGS. 9 and 10. Waist band 52 is much wider than that of normal panties since it fits around the wide part of the hip (not at the waist). Height h is much lower than normal panties. Leg holes 56 complete the configuration.

If the user is wearing pants, she may use version 50 (FIG. 9) with adhesive patches 54 attached to the outside surface of garment 51. In this case, garment 51 would be secured to the outer garment (pants).

Alternatively, version 60 (FIG. 10) may be worn with any type of outer garment wherein adhesive patches 64 are inward facing to attach to the user's skin. A single garment 51 can be supplied with four adhesive patches (or fewer) each with adhesive and release liners on both surfaces. In this manner, the patches can be attached to either the inner surface of garment 51 (FIG. 10) or to the outer surface (FIG. 9) as desired. Disposable or reusable versions can be fabricated as described in the summary.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing from the scope of the invention.

What is claimed is:

1. A panty line free undergarment apparatus comprising:
   a thin absorbent pad being mounted upon an elongated thin, stretch fabric strap;
   said thin absorbent pad having a thickness up to 1 mm:
   said elongated thin, stretch fabric strap being of substantially uniform width over a whole length thereof, said pad being mounted upon an elongated thin, stretch fabric strap by an adhesive on a central portion of, and on one side of, said strap;
   said stretch fabric strap having a removable adhesive patch on a front end and a further removable adhesive patch on a rear end thereof for attaching said strap to the skin of a user so that said pad covers a lower orifice of said user;
   respective undersides of each adhesive patch having a nonallergenic adhesive covered by a release liner which is removed prior to attachment to the skin of the user; and
   said thin strap and thin pad presenting no visible appearance of lines through the user's clothing; and wherein said thin pad allowing some absorbency of body moisture and residual excretions.

2. The disposable panty line free undergarment apparatus as in claim 1 further comprising:
   an infusion of fragrance within the undergarment apparatus.

3. The disposable panty line free undergarment apparatus of claim 1 in which said pad is disposable and said strap is washable and reusable.

* * * * *